US010973438B2

(12) United States Patent
Mathiasmeier et al.

(10) Patent No.: US 10,973,438 B2
(45) Date of Patent: Apr. 13, 2021

(54) CAPACITANCE MEASURING AND IMAGING SENSOR SYSTEM

(71) Applicants: Michael L. Mathiasmeier, Houston, TX (US); Dwayne Leroy Mason, Houston, TX (US)

(72) Inventors: Michael L. Mathiasmeier, Houston, TX (US); Dwayne Leroy Mason, Houston, TX (US)

( * ) Notice: Subject to any disclaimer, the term of this patent is extended or adjusted under 35 U.S.C. 154(b) by 0 days.

(21) Appl. No.: 17/021,509

(22) Filed: Sep. 15, 2020

(65) Prior Publication Data

US 2020/0405186 A1 Dec. 31, 2020

Related U.S. Application Data

(63) Continuation of application No. 15/677,012, filed on Aug. 15, 2017, now Pat. No. 10,772,536.
(Continued)

(51) Int. Cl.
| | |
|---|---|
| *G01R 27/26* | (2006.01) |
| *A61B 5/107* | (2006.01) |
| *A61B 5/0536* | (2021.01) |
| *G01B 7/02* | (2006.01) |

(Continued)

(52) U.S. Cl.
CPC .......... *A61B 5/1074* (2013.01); *A61B 5/0536* (2013.01); *A61B 5/7225* (2013.01);
(Continued)

(58) Field of Classification Search
CPC ... A61B 5/1074; A61B 5/0536; A61B 5/7225; A61B 5/743; A61B 5/053; A61B 2562/0214; A61B 2576/02
(Continued)

(56) References Cited

U.S. PATENT DOCUMENTS

| | | | |
|---|---|---|---|
| 2,216,533 | A | 10/1940 | Kaplan |
| 3,328,882 | A | 7/1967 | Blivice |

(Continued)

FOREIGN PATENT DOCUMENTS

| | | |
|---|---|---|
| EP | 284922 | 10/1988 |
| EP | 285989 | 10/1988 |
| WO | 99/20179 | 4/1999 |

*Primary Examiner* — Farhana A Hoque
*Assistant Examiner* — Courtney G McDonnough
(74) *Attorney, Agent, or Firm* — Greenberg Traurig, LLP; Dwayne L. Mason

(57) ABSTRACT

Embodiments herein provide methods, apparatus and computer systems comprising an input unit for inputting one or more data sets to be processed comprising a capacitance measuring device configured to measure one or more conductive elements on a sensor plane and provide a corresponding data set of measurements obtained from the conductive elements. A computing unit is coupled to the input unit and for processing the data sets; the computing unit comprises at least one processor with non-transient memory. An output unit is connected to the computing unit for outputting data received from the computing unit. A computer program stored in memory comprising instructions that cause the computer to isolate and discharge conductive and reference impedance elements, perform a charge transfer to the one or more conductive elements on the sensor plane, measure the relative difference between the conductive elements and reference impedance element, and store measurements in non-transient memory.

20 Claims, 11 Drawing Sheets

Related U.S. Application Data

(60) Provisional application No. 62/374,884, filed on Aug. 14, 2016.

(51) Int. Cl.
*A61B 5/00* (2006.01)
*A61B 5/053* (2021.01)

(52) U.S. Cl.
CPC ............... *A61B 5/743* (2013.01); *G01B 7/02* (2013.01); *A61B 5/053* (2013.01); *A61B 2562/0214* (2013.01); *A61B 2576/02* (2013.01)

(58) Field of Classification Search
USPC ........................................................ 324/671
See application file for complete search history.

(56) References Cited

U.S. PATENT DOCUMENTS

| | | |
|---|---|---|
| 3,457,647 A | 7/1969 | Cohen et al. |
| 4,294,014 A | 10/1981 | Baumann et al. |
| 4,734,034 A | 3/1988 | Maness et al. |
| 5,123,169 A | 6/1992 | White et al. |
| 5,128,880 A | 7/1992 | White |
| 5,323,650 A | 6/1994 | Fullen et al. |
| 5,361,133 A | 11/1994 | Brown et al. |
| 5,729,905 A | 3/1998 | Mathiasmeier |
| 5,790,256 A | 8/1998 | Brown et al. |
| 6,029,358 A | 2/2000 | Mathiasmeier et al. |
| 6,546,356 B1 | 4/2003 | Genest |
| 6,621,013 B2 | 9/2003 | Tanida et al. |
| 6,741,728 B1 | 5/2004 | Genest |
| 6,879,945 B1 | 4/2005 | Cook |
| 7,089,152 B2 | 8/2006 | Oda et al. |
| 7,433,502 B2 | 10/2008 | Rutschmann |
| 7,489,813 B2 | 2/2009 | Rutschmann et al. |
| 8,482,743 B2 | 7/2013 | Segev |
| 9,019,359 B2 | 4/2015 | Leedy et al. |
| 9,402,567 B2 | 8/2016 | Danenberg et al. |
| D824,270 S | 7/2018 | Mathiasmeier |
| 10,772,536 B2 | 9/2020 | Mathiasmeier |
| 2008/0042660 A1 | 2/2008 | Ely et al. |
| 2012/0268416 A1 | 10/2012 | Pirogov et al. |
| 2014/0132287 A1 | 5/2014 | Reynolds et al. |
| 2018/0140226 A1 | 5/2018 | Mathiasmeier |

CAPACITANCE MEASURING AND IMAGING SENSOR SYSTEM

CROSS-REFERENCE TO RELATED APPLICATIONS

This application is a continuation of U.S. Non-Provisional application Ser. No. 15/677,012 filed on Aug. 15, 2017, which claims the benefit and priority benefit, of U.S. Provisional Application Ser. No. 62/374,884 filed on Aug. 14, 2016, the contents of which are incorporated by reference herein in their entirety.

STATEMENT REGARDING FEDERALLY SPONSORED RESEARCH OR DEVELOPMENT

Not applicable.

BACKGROUND

Footcare products, such as shoes and orthotics, may be time consuming to fit because feet are variable in size. It would be beneficial of feet could be measured efficiently such that there is a small chance of errors when fitting footcare products to individuals' feet. While molds and lasts can be accurate, they may be time consuming and not easily transferable to many people. It would be advantageous to provide a method and system that measures for footcare products very quickly and may be applied to individual needs.

BRIEF SUMMARY

The following presents a simplified summary of the disclosed subject matter in order to provide a basic understanding of some aspects of the subject matter disclosed herein. This summary is not an exhaustive overview of the technology disclosed herein. It is not intended to identify key or critical elements of the disclosed embodiments or to delineate the scope of the disclosed embodiments. Its sole purpose is to present some concepts in a simplified form as a prelude to the more detailed description that is discussed later.

Presented herein is a system and method which discerns physical characteristics, including but not limited to the general shape, outline, length, width, girth, cross section, pressure gradient, permittivity, current, capacitance, conductance, resistance etc. of a reactive impedance material, including its, and other physical data associated with reactive impedance material. Images and physical characteristics of reactive impedance material (dielectric, conductive, capacitive, inductive, etc. material) such as anything in, on or associated with the anatomy of a human or animal body can be ascertained with the systems and methods disclosed herein. This is achieved in a preferred embodiment using a solid-state system comprised of a distributed capacitance sensing surface, multiplexer circuit, controller, signal processing circuit, memory, display and power module which measures the capacitance of a reactive impedance material displaced on or adjacent to the sensing surface.

Embodiments of the present invention provide a portable and user-friendly, self-serve measuring device. Specifically, in one embodiment the measuring device may be free of moving parts and automatically provides physical data, such as user shoe size and/or basic orthopedic data, when a reactive impedance material is adjacent to or comes in contact with or in a region of a measurement or sensing area associated with the measuring device without requiring additional user intervention. This is achieved in a preferred embodiment using a digitally controlled device equipped with a sensor plane, control unit, memory, display and power module which measures the capacitance in areas within the sensor plane to discern the physical data of a reactive impedance material. In the case of a foot, this comprises the length, width and/or outline as well as the relative pressures exerted by the force of the foot at various points within or near the sensor plane. Certain of the generated data can be used to generate and image of the reactive impedance material.

BRIEF DESCRIPTION OF THE DRAWING

For a more complete understanding of this disclosure, reference is now made to the following brief description, taken in connection with the accompanying drawings and detailed description, wherein like reference numerals represent like parts.

Figure 1A:
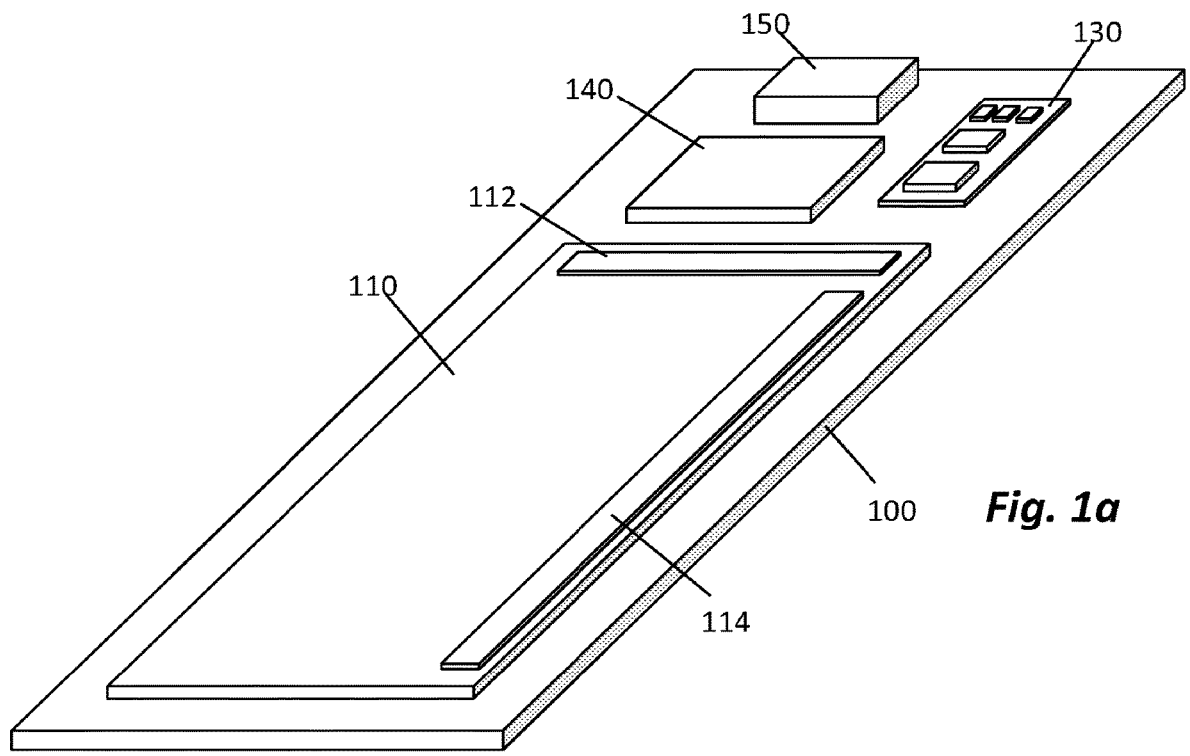
FIG. 1a illustrates a physical layout of a preferred embodiment.

While certain embodiments will be described in connection with the preferred illustrative embodiments shown herein, it will be understood that it is not intended to limit the invention to those embodiments. On the contrary, it is intended to cover all alternatives, modifications, and equivalents, as may be included within the spirit and scope of the embodiments as defined by claims. In the drawing figures, which are not to scale, the same reference numerals are used throughout the description and in the drawing figures for components and elements having the same structure.

DETAILED DESCRIPTION

It should be understood that, although an illustrative implementation of one or more embodiments are provided below, the various specific embodiments may be implemented using any number of techniques known by persons of ordinary skill in the art. The disclosure should in no way be limited to the illustrative embodiments, drawings, and/or techniques illustrated below, including the exemplary designs and implementations illustrated and described herein. Furthermore, the disclosure may be modified within the scope of the appended claims along with their full scope of equivalents.

Figure 1B:
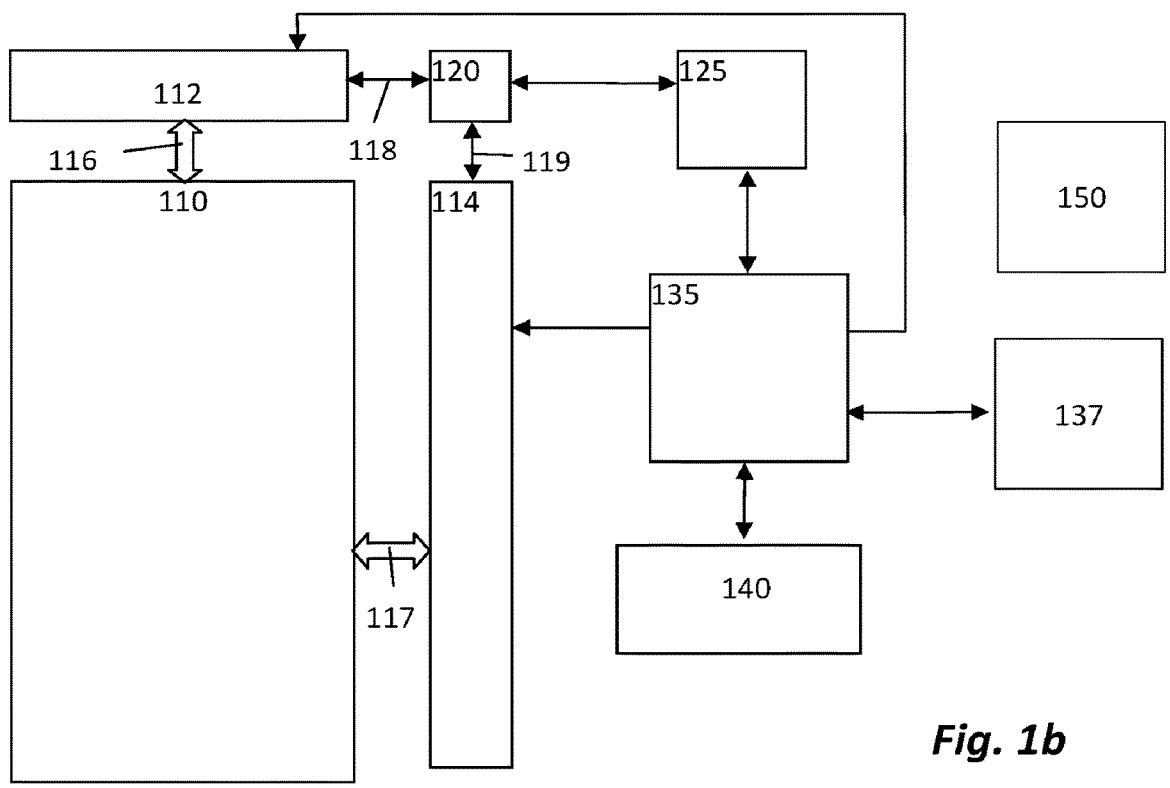
FIG. 1b illustrates a block diagram of a preferred embodiment.

As shown in FIG. 1a and FIG. 1b, a preferred embodiment includes a sensor plane 110, horizontal 114 and vertical 112 multiplexer circuits, controller and signal processing circuitry 130, display 140 and power module 150 all placed within a housing or substrate 100. The circuitry module 130 contains the controller 135, memory 137, signal processor 125 and reference impedance element 120 and supporting circuitry. The signal processor 125 contains an analog/digital converter (ADC), digital/analog converter (DAC), internal switch for connecting either the ADC or DAC to the reference impedance element 120 and communication circuitry for communicating with controller 135. Display 140 may be a read only display or a touch screen which may serve as a user interface allowing the user to direct device operation as well as read measurement results. Power module 150 serves as the power supply for the device to supply energy for the multiplexers 112, 114, circuitry module 130 and display 140. Although a battery may be used with a preferred embodiment, other options may include a power entry jack for an external power supply or photovoltaic cell. Lastly, it is noted that many physical configurations of such components are possible and thus a preferred embodiment shown in FIG. 1a is presented only for illustration. Further, with the wide variety of packages and multi-functionality available with modern semiconductor devices, it is assumed apparent to one skilled in the art of electrical design that the physical circuit layout of FIG. 1a with a preferred embodiment represents but one of many realizations of the block diagram of FIG. 1b. For example, the reference impedance element 120, signal processor 125, controller 135 and memory may be separate discrete circuits or may all be integrated within a common device.

Figure 2:
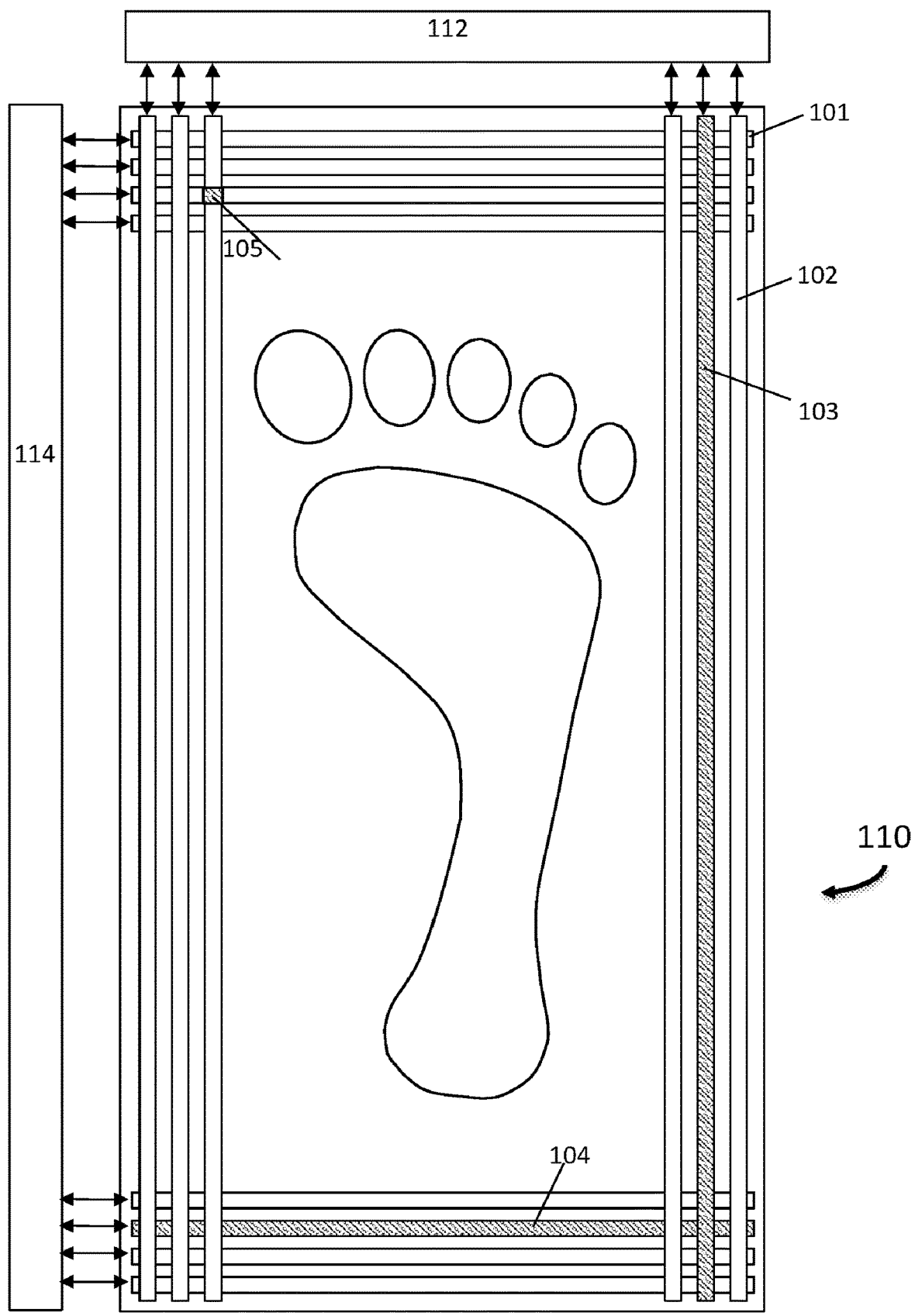
FIG. 2 illustrates a block diagram of a sensor plane.

As shown in FIG. 2, the sensor plane 110 is constructed of a non-conductive sheet containing a series of electrically isolated horizontal conductive elements 101 and vertical conductive elements 102 extending the height and width of the sensor plane 110. The sensor plane may be planar as may be embodied in a traditional rigid printed circuit board or in any other arrangement, e.g., a flexible sensor plane that can be made into various geometric shapes, e.g., tubular, square, rectangle, etc. Note, although FIG. 2 shows only select conductive elements for clarity, one or more elements may be used within an actual embodiment to extend contiguously with uniform element density across the width and height of the sensor plane 110. Also, it is further noted that a preferred embodiment may include realizing conductive elements 101, 102 as solid conductive traces positioned on opposite sides of the sensor plane sheet 110 as disclosed in FIG. 2 and FIG. 5a, and as a collection of horizontally connected and vertically connected rows and columns of pads all residing within the same plane as pictured in FIG. 5b, as well as other geometric arrangements suitable for the desired reactive impedance material to be measured or imaged. With the pad configuration, pads within the same row 101 or column 102 are electrically connected with rows and columns being electrically isolated. An advantage of this design is that it allows the surface area of both row and column conductive elements to be positioned directly adjacent to the sensed medium without the overlapping of rows and columns that occurs with the solid element construction thereby preventing obstruction and affords better capacitance measurement.

Figure 3:
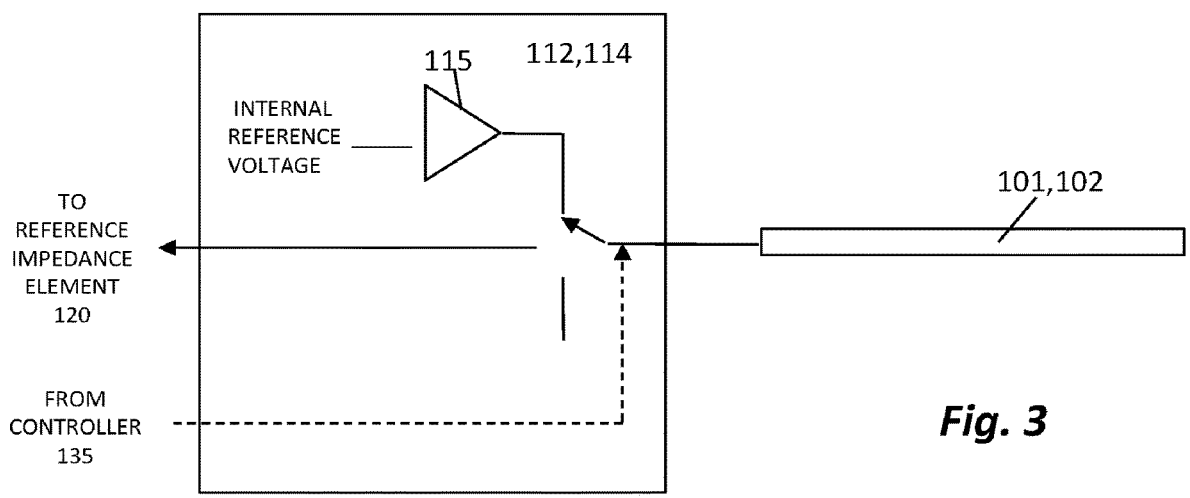
FIG. 3 illustrates a schematic of an internal multiplexer switch configuration.

As further shown in FIG. 2, each of the one or more horizontal 101 and vertical 102 conductive elements are connected to one or more horizontal 114 and vertical 112 multiplexer circuits, respectively, which in turn, can channel one or more of said elements 101, 102 to the reference impedance element 120. As shown in FIG. 3, the multiplexer circuits are of programmable solid-state construction under direction of controller 135 such that connections to each element 101, 102 may be connected to the output of either a buffer circuit 115 allowing said element 101, 102 to be driven to a specified voltage level, connected directly to the reference impedance element 120 or electrically disconnected from the multiplexer as a high impedance.

Figure 4:
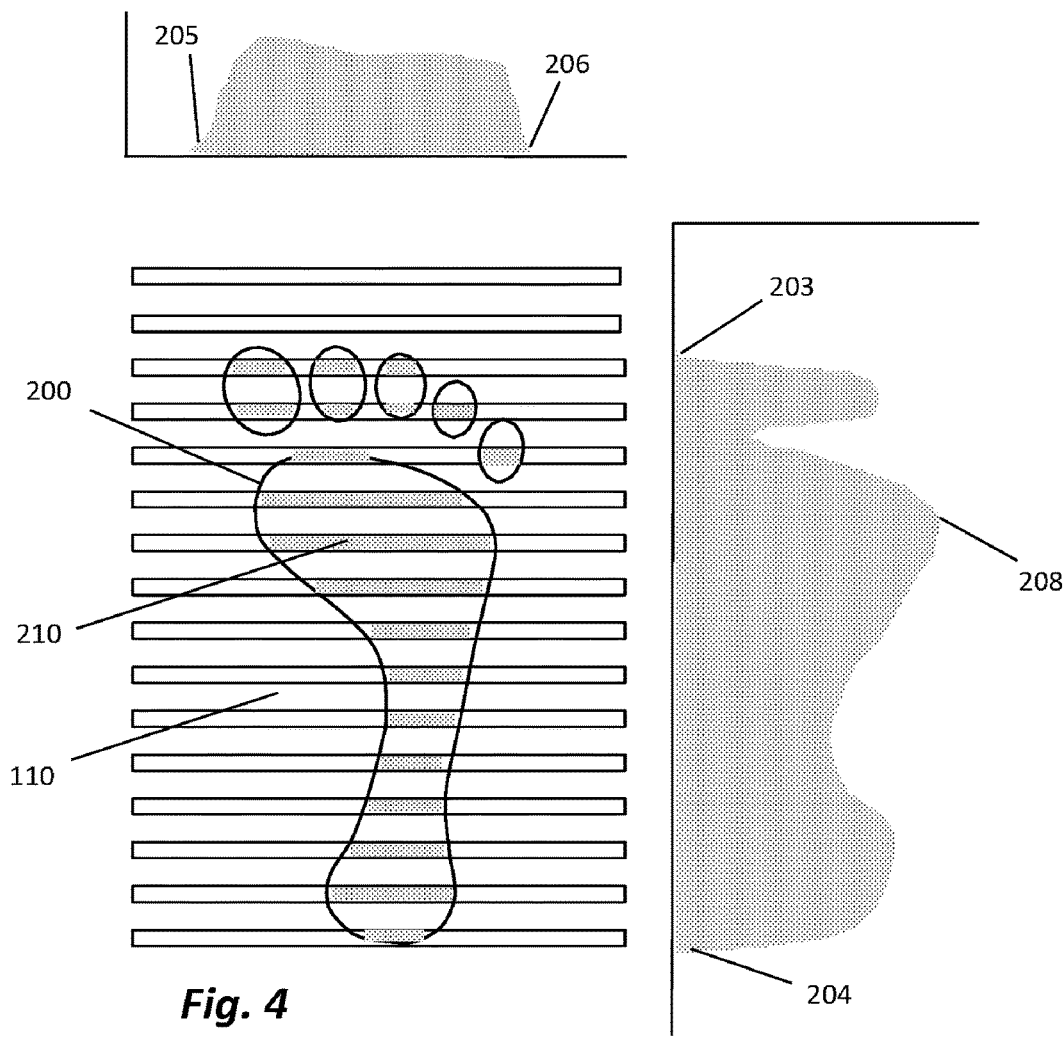
FIG. 4 illustrates permittivity distribution across a sensor plane.

With reference to FIG. 4, measurement of a reactive impedance material, here the foot pattern 200, is achieved by placing a foot on or adjacent to the sensor plane 110 and measuring the capacitance between the conductive elements 101, 102 and the surrounding medium adjacent to the sensor plane 110 at a subset of specific regions within the sensor plane surface. The human body is roughly 70% water and the permittivity of water is roughly 80 times that of air, so human body material, e.g., a foot 200, present on or adjacent to the sensor plane 110 will increase the local permittivity and hence the available electrical charge where it comes into contact with or adjacent to said plane as represented by the shaded areas (e.g. 210) and permittivity profiles shown in FIG. 4. This allows for a 2D image of the reactive impedance material, here the foot, to be constructed based on the charge distribution or capacitance values recorded by this embodiment across the sensor plane surface.

Figure 5A:
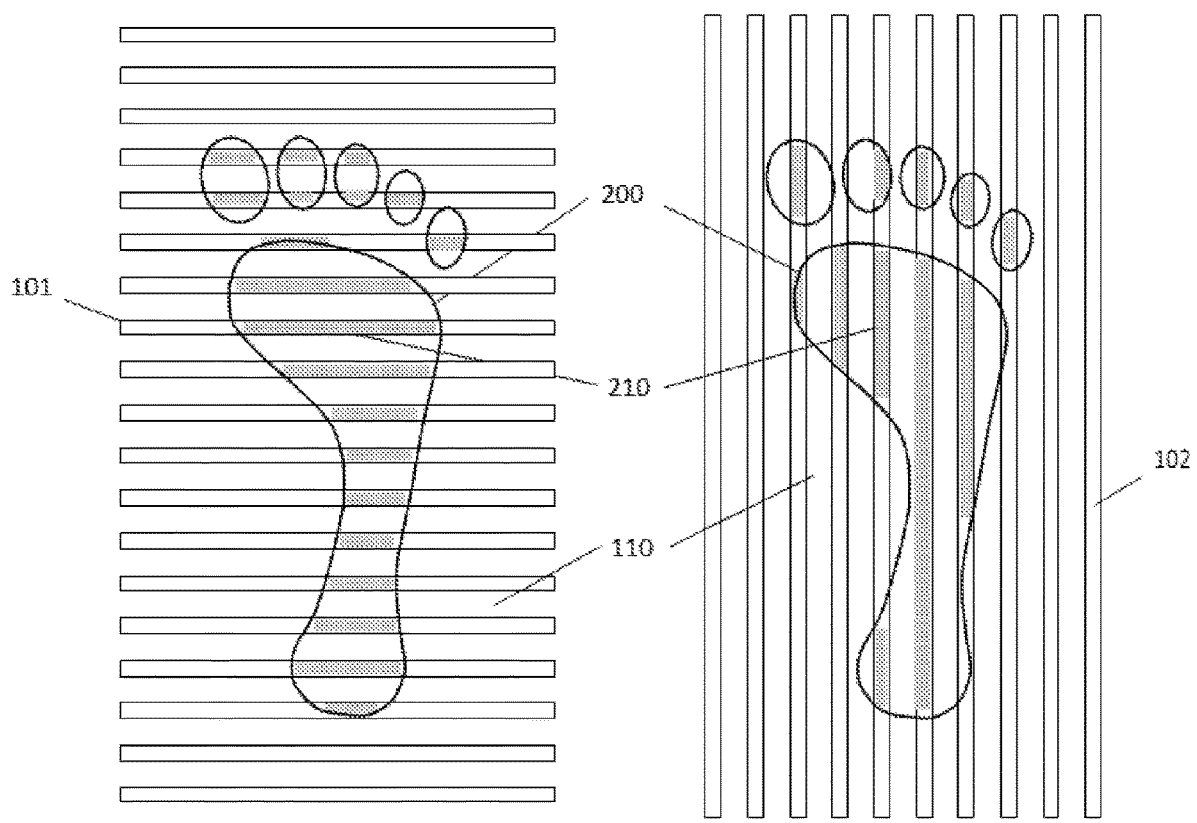
FIG. 5a illustrates a layout of conductive elements used to determine foot length and width.
Figure 5B:
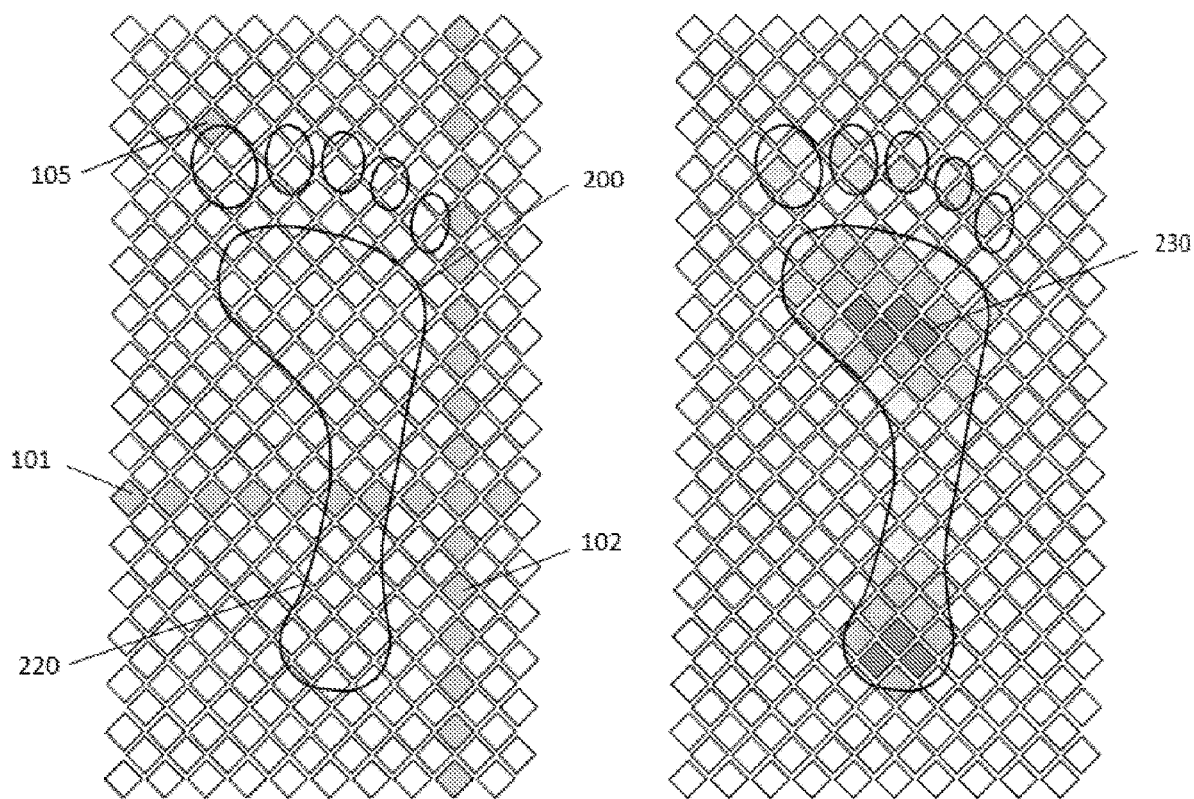
FIG. 5b illustrates a layout of conductive elements used to image foot contour and pressure gradient.

Preferred embodiments use one or more measurement protocols based on the data. As illustrated with respect to FIG. 5a, a first type technique utilizes the horizontal conductive elements 101 and multiplexer 112 and vertical conductive elements 102 and multiplexer 114 separately to measure the length and width, respectively, as shown. This technique requires relatively fewer data points, is faster, and is suitable where limited data is sufficient for providing a shoe size estimate to facilitate footwear selection. The second technique as shown in FIG. 5b is a higher resolution scan which uses both horizontal 101 and vertical conductive elements 102 together to measure the capacitance at specific points 105 contiguously across the entire surface 110. Here it is noted that contact areas of greater pressure resulting from less curvature of a reactive impedance material, e.g., the foot, and greater normal force component serve to press the reactive impedance material surface closer to the sensor plane surface 110 decreasing the air gap between the two. This effectively increases the capacitance and resulting charge providing a 2D map or pressure gradient of the foot surface as shown in FIG. 5b. Thus, the latter method measures not only the length and width of the reactive impedance material, e.g., the foot 200, but also the contour or outline 220 as well as the overall pressure gradient 230 making up the surface of the entire reactive impedance material, e.g., foot 200. The pressure gradient may be displayed differentially by color and/or shade. This affords additional information which in the case of a foot, aside from estimating shoe size, may also be used with podiatry services to design custom footwear or orthotics.

Capacitance measurements are conducted in the same way using both techniques with only the region defined by the conductive element 101, 102, 105 selections defining the measurement protocol. It should be understood that according to the embodiments disclosed herein, most any method for measuring capacitance such as measuring resonant frequencies, amplitude at specified frequencies, charging and discharging times as are commonly employed in electronic design may be used. However, a preferred embodiment may employ a charge transfer technique due to its potential for high noise immunity. Here, values are measured relative to the charge stored in the reference impedance element 120. First, the reference impedance element and all conductive elements 101, 102 are grounded relative to the system power supply via a switch setting within the signal processor 125 and setting the multiplexer internal voltage to ground and connecting all multiplexer outputs to the buffer 115 configuration as directed in software within controller 135 and communicated to multiplexers 112, 114 and signal processor via standard communication protocols and hardware commonly used in the art such as I2C, SPI or dedicated communication pins depending upon the controller and multiplexer chips and packages utilized. Here, the multiplexers 112, 114 connections 118, 119 to the reference impedance element 120 are left in the open or high impedance state thus isolating element 120 and completely discharging it, as well as all conductive elements 101, 102. Next, a single selected element 101 is made high by programming the associated internal pin buffer voltage 115 of the accompanying multiplexer 112 to a high positive voltage level under direction of controller 135, software. After a sufficient time delay to allow for charge equalization, the conductive element 101 will be fully charged and reference impedance element 120 will be fully discharged. At this point, both the conductive element 101 and impedance element 120 are shorted together by placing both multiplexer switch connections 117, 119 in the pass through or closed position allowing charge to drain from the conductive element 101 to the impedance element 120 until the electric potential across both elements are equal. From basic electrical theory we have $$Q = C_C V_H \qquad (1)$$

where Q is the charge across the conductive element 101, $C_C$ is its capacitance and $V_H$ is the high level multiplexer voltage 115. Since charge is conserved, it will be distributed across both the conductive element 101 and reference element 120 upon shorting them together which gives $$Q = C_C V_H = (C_C + C_R) V_R \text{ or } V_R = C_C V_H / (C_C + C_R) \qquad (2)$$

where $V_R$ is the voltage across the reference impedance element 120 and $C_R$ is the capacitance of the reference impedance element 120. Further, if it is assumed that the reference impedance element capacitance $C_R$ is much greater than $C_C$, equation 2 can be simplified as $$V_R = C_C V_H / C_R \qquad (3).$$

Although this last simplification is not necessary for operation, it emphasizes the fact that upon completion of the measurement process, the voltage $V_R$ across the reference impedance element 120 is a function of the conductive element capacitance $C_C$. This voltage is then digitized using the ADC of the signal processing circuit 125 and stored within the controller memory 137. Lastly, although also unnecessary for operation, common mode distortion may be reduced improving the signal to noise ratio (SNR) by reversing the procedure described above to obtain a differential signal. That is, the reference impedance element 120 is first fully charged and the conductive element 101 discharged. The resulting measurement is then taken as the difference between both measurements thus cancelling out any common mode bias In accordance with a preferred embodiment, it is noted that regardless of the measurement scenario, raw data is also translated and scaled to remove biases caused by manufacturing and material anomalies and normalize readings to compensate for variances in sensitivity and the permittivity of reactive impedance material samples. Initially, the device is calibrated by making a first reading in all element values 101, 102, 105 are measured with no reactive impedance material sample present on or adjacent to the sensing surface 110. These values are then stored as a data array in memory 137 and retained as reference values which are subtracted from all future active measurements. Secondly, all values within said array are scaled by a factor to set the maximum measured value equal to a desired standard. Thus, biases are removed from raw data and it is adjusted to be relatively uniform and immune to anomalies in sensor plane and sample characteristics.

This technique is used directly with the first measurement protocol described above. Here, charge transfer is used in conjunction with a self-capacitance method of distributed capacitance measurement. Here, horizontal conductive elements 101 are contiguously activated from the top to the bottom of sensor plane 110 using multiplexer 112 under direction of controller 135. The measured voltage appearing across the reference impedance element 120 by the signal processing circuit 125 is recorded and stored in memory 137 for each of the horizontal elements 101 producing a capacitance or permittivity profile as shown in FIG. 4. To obtain the length of reactive impedance material, here foot 200, the values of said profile are simply assessed from top to bottom and from bottom to top. The first value in a top to bottom scan that exceeds a trip point indicating the presence of a high permittivity object may be recorded as the toe or the top of the foot 203. Similarly, the first such value detected in a bottom to top scan is recorded as the heel or bottom of the foot 204. Lastly, the overall length is obtained by multiplying the number of conductive elements 101 between the toe and heel marks by their center-to-center distance. The same procedure is used to determine the foot 200 width using the conductive elements 102 and multiplexer 114 as shown in FIG. 5*a*. Here scans are made from left to right and right to left looking for said base set points discerning the left 205 and right 206 most edges of the foot 200. The width is then calculated by multiplying the number of conductive elements 102 between the left and right edges by their center-to-center distance. Once the foot length and width are known in conventional units of measure, this information can then be applied to the sizing systems of the various shoe sizing scales to estimate the closest shoe size which may be presented on display 140 via controller 135. Lastly, it is noted some shoe sizing scales also use the location of the ball of the foot in addition to the overall length and width to determine the size. Here it has been discovered as noted and shown in FIG. 4 that the ball most often is the meatiest part of the foot which produces a local maxima or peak 208 directly after the toe in the permittivity profile. Thus, to find the ball location one merely searches the length array obtained earlier for the peak or maximum value occurring between the toe and half way through the length of the foot.

A second method of foot measurement shown in FIG. 5*b* also uses charge transfer. However, here, specific pads or intersections of rows and columns 105 are selected for measurement rather than an entire row 101 or column 102. This achieved in a similar way as for the previous measurement protocol except one dimension, either row or column, is dedicated to a driving task injecting either the high or low voltage across the element 101, 102, while the opposite dimension is assigned a receiving task and is connected directly to the reference impedance element 120. In this way, the entire sensor plane 110 can be scanned and the capacitance measured at each pad or intersection of rows and columns 105 producing a 2D array of data points and a resulting pressure gradient as shown in FIG. 5b. For the purpose of illustration we can assign the vertical elements 102 and multiplexer 114 the driving role and the horizontal elements 101 and multiplexer 112 the receiving role successively tying each horizontal element 101 to the reference impedance element 120. In scanning from left to right, the left most vertical element 102 is set to a high voltage and fully charged as previously described while the reference impedance element 120 is isolated and discharged under direction of controller 135. Next, the reference impedance element 120 is then connected to the horizontal element 101 allowing element 102 to discharge into the reference element 120 across the capacitive junction established by the combination of adjacent pads at the intersection of elements 101, 102 and the foot 200, if present. Finally, after a sufficient time delay to allow for the charge to equalize, the voltage $V_R$ across the reference impedance element 120 is measured by the signal processing circuitry 125 and stored in memory 137 all under direction of controller 135 as previously described regarding the general charge transfer process. Then this same process is repeated for each of the horizontal elements 101 with each producing a reference element voltage representative of the capacitance at the point of intersection between vertical element 102 and horizontal element 101. Finally, this process is again repeated, independently scanning all horizontal elements 101 for each of the remaining vertical elements 102 producing a 2D array of data points covering the entire sensing plane 110 producing a total number of points equal to the number of intersecting points or the product of the number of vertical and horizontal elements.

Figure 5C:
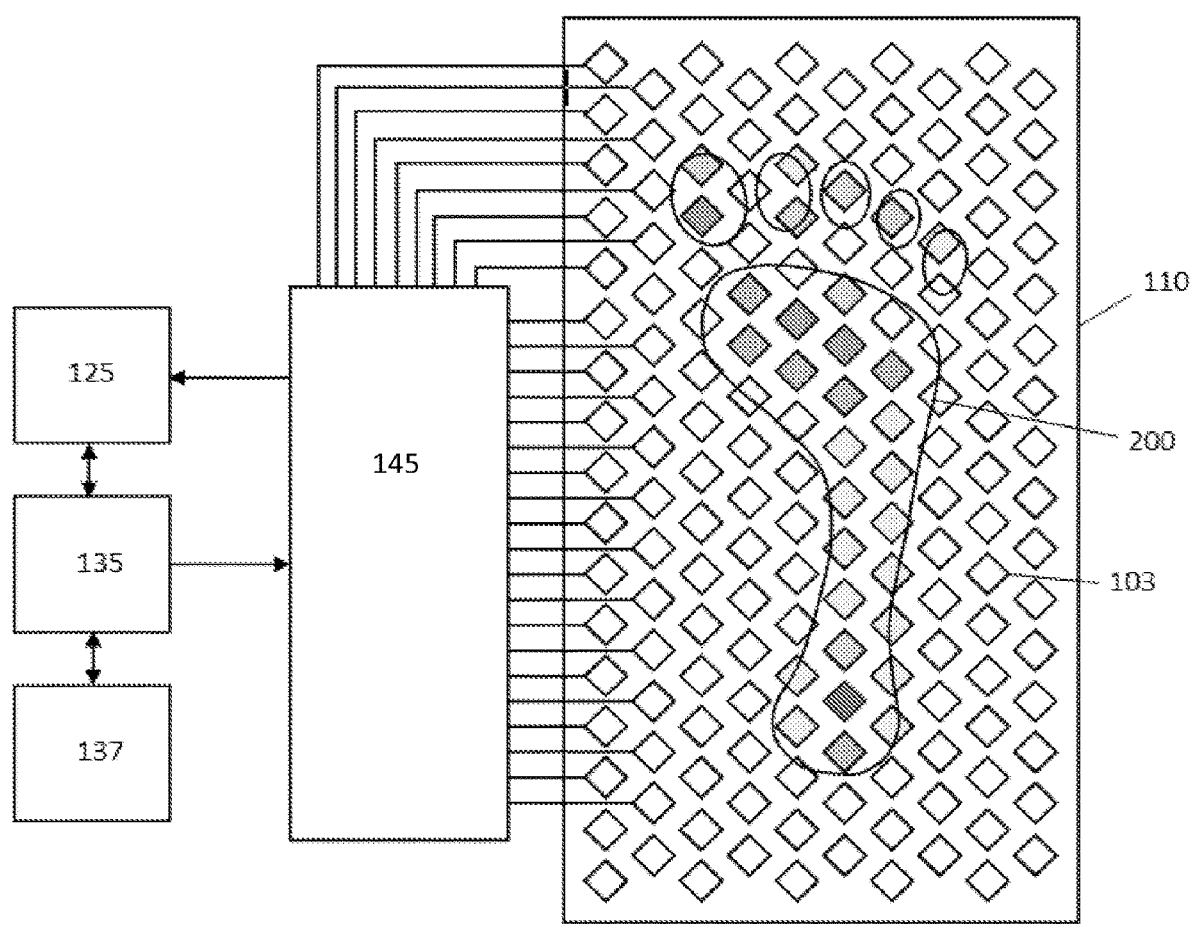
FIG. 5c illustrates two dimensional self-capacitance foot imaging.

As illustrated in FIG. 5c, still another preferred embodiment includes the use of a two dimensional grid of capacitance sensor elements 103 connected independently to multiplexer circuit 145 as shown schematically. This circuit leverages the benefits of other disclosed embodiments in that it possesses the enhanced sensitivity of the self capacitance design of FIG. 5a, while providing the two dimensional sensing of FIG. 5b. Here, conductive elements 103 are contiguously activating individually from left to right and top to bottom across sensor plane 110 using multiplexer 145 under direction of controller 135. In a process analogous to that discussed with FIG. 5a, the self capacitance of each sensor element is indirectly measured by measuring the voltage appearing across the reference impedance element 120 by the signal processing circuit 125 and storing the result in memory 137, producing a two dimensional capacitance or permittivity map represented by the gray scale intensity of the sensor elements 103 as shown in FIG. 5c. While there is an increase in multiplexer connections, which increases in proportion to the second order of sensor board dimensions, it may be advantageous for use in noisy or low sensitivity applications where the higher sensitivity of self capacitance is required. It is also noted that for clarity of presentation, only a portion of the multiplexer connections are illustrated and it is assumed obvious to one trained in the art that each and every conductive element 103 present within the 2D array of sensor plane 110 requires a separate and independent ground referenced connection to multiplexer 145. That is, in essence, the sensing of the one and two dimensional self capacitance arrays of FIG. 5a and FIG. 5c function in exactly the same way with the number, geometry and spatial arrangement of conductive elements 101,102, and 103 being the only difference. Also as will be understood to one trained in the art that although only a single multiplexer 145 and signal processor 125 with integral analog to digital converter is shown, any number of multiple multiplexers and/or signal processors and scanning orders may be used without diverting from the novel element of the invention presented. This serves to divide the sensing plane into subsections which may be simultaneously scanned in parallel to increase overall board scanning rate. Also, while conductive elements may be sampled contiguously, there is no requirement in the embodiments disclosed herein that the adjacent elements must sampled sequentially and other sampling methods such as compressive sensing may be used.

Figure 6:
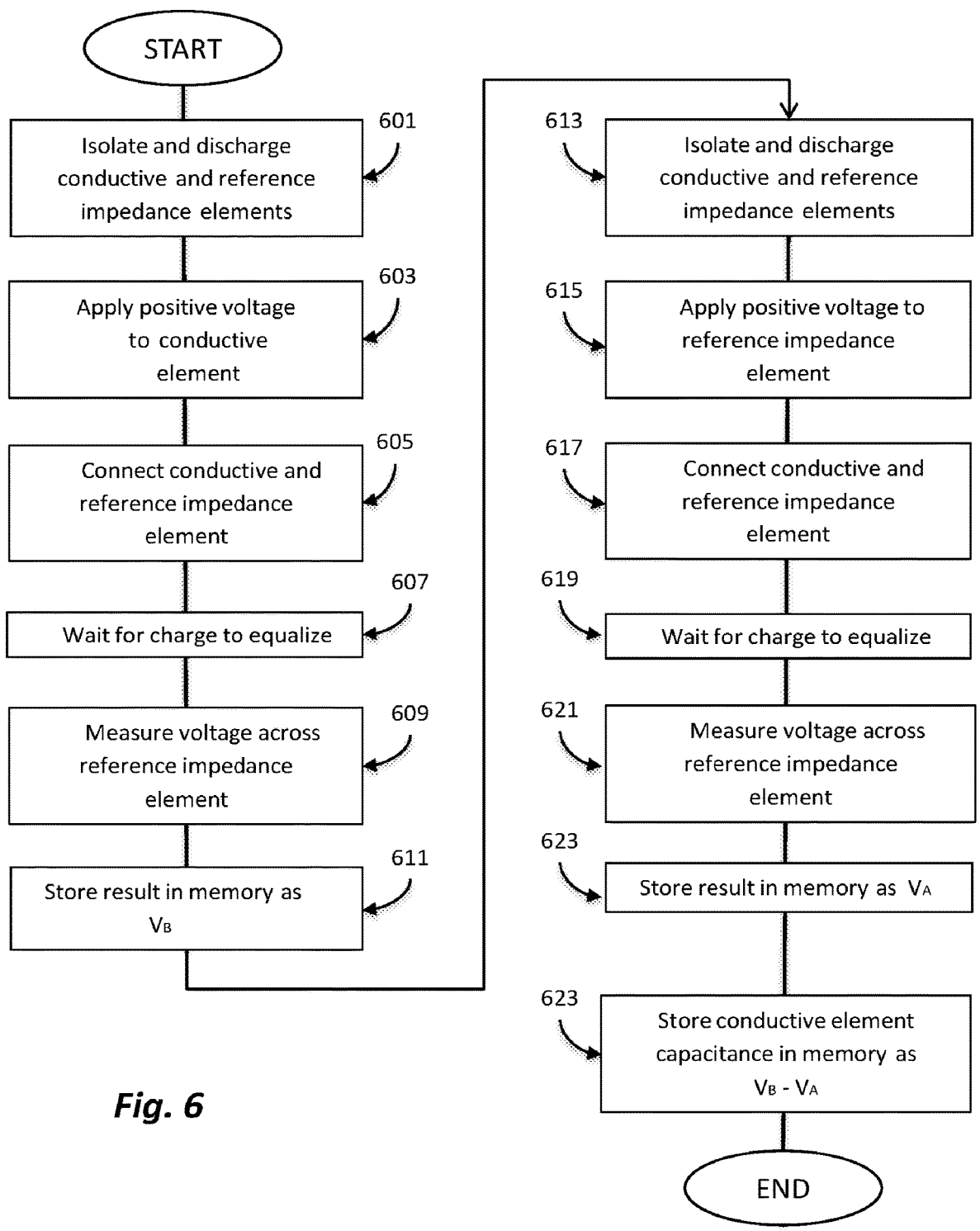
FIG. 6 illustrates a flow diagram of a charge transfer capacitance measurement method according to the present disclosure.

FIG. 6 is a flow chart of charge capacitance measurement that begins with isolating and discharging 601 conductive and reference impedance elements. A positive voltage is applied 603 to a conductive element and then the conductive and reference impedance elements are connected 605. The charge is equalized 607 and the voltage across the reference impedance element is measured 609. The measurement is stored in memory as $V_B$ 611. Then measurement process continues by discharging 613 conductive and reference impedance elements. A positive voltage is applied 615 to a reference impedance element and then the conductive and reference impedance elements are connected 617. The charge is equalized 619. The voltage across the reference impedance element is measured 621 and the result is stored in memory as $V_A$ 623. The conductive element capacitance, $V_B$-$V_A$, is stored in memory 625.

Figure 7:
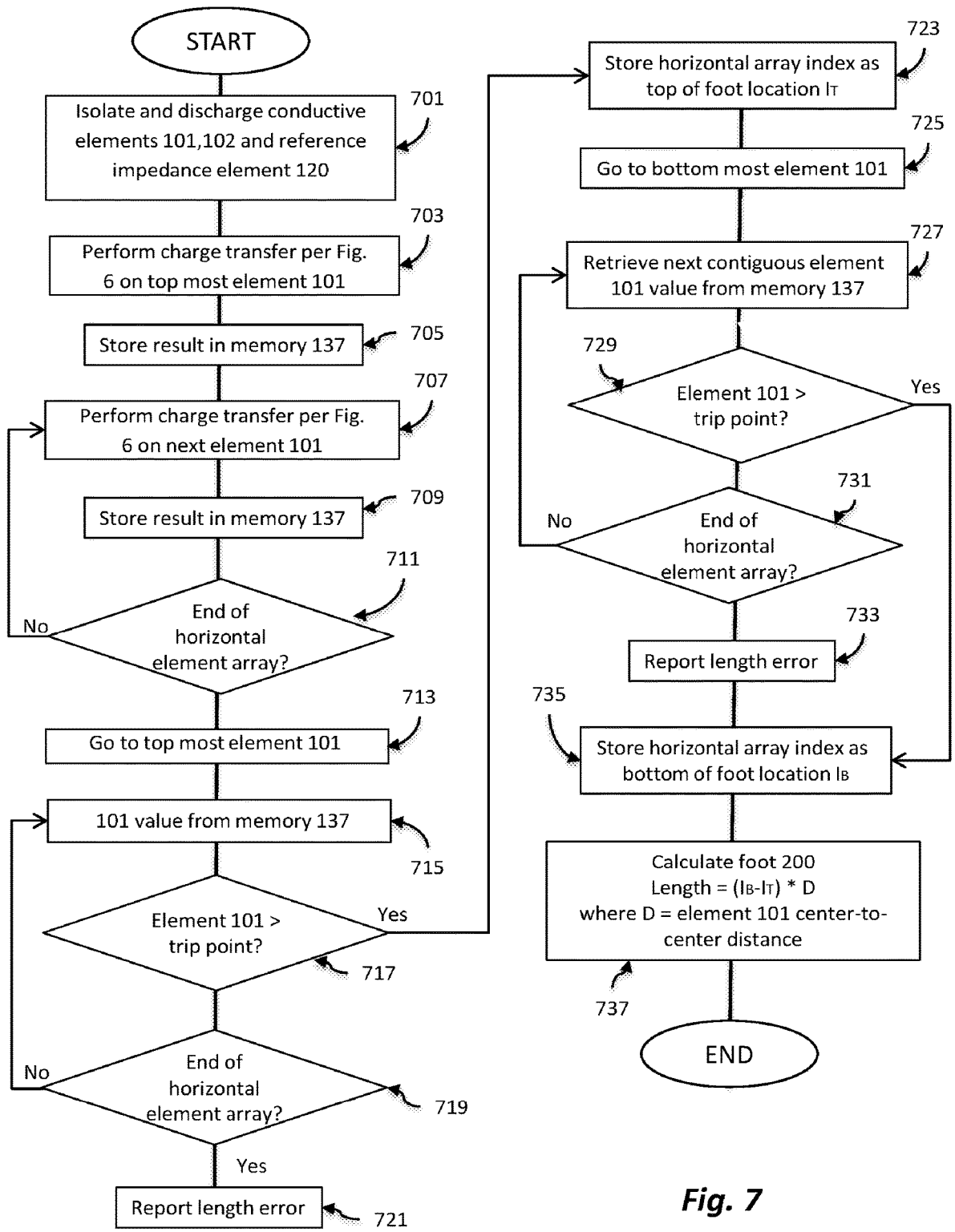
FIG. 7 illustrates a flow diagram of a length measurement algorithm according to the present disclosure.

FIG. 7 is a flow diagram for length measurement. The method begins with isolating and discharging conductive elements 701 and the reference impedance element 120. A charge transfer 703 per FIG. 6 is performed on the first element 101. This result is stored in memory 705. A charge transfer 707 per FIG. 6 is performed on the next element 101, and that result stored 709 in memory. If all elements of the horizontal array are not sampled 711, the method reverts to performing a charge transfer (707). Otherwise the method proceeds to the top most element 101 at 713 and retrieves the 101 value from memory 715. When element 101 is greater than a trip point at 717, the method proceeds to store horizontal array index as top of foot location $L_T$ 723. Otherwise the method proceeds through the horizontal array unless there is an error 721. After storing horizontal array index, go to bottom most element 101 at 725, then proceed through elements 101 from memory 727. Again when element 101 is greater than trip point 729, horizontal array index is stored as bottom of foot location $L_B$ 735. Otherwise the horizontal array elements are continued to be sampled 731. The foot length is then determined 737 as $L_T$-$L_B$.

Figure 8:
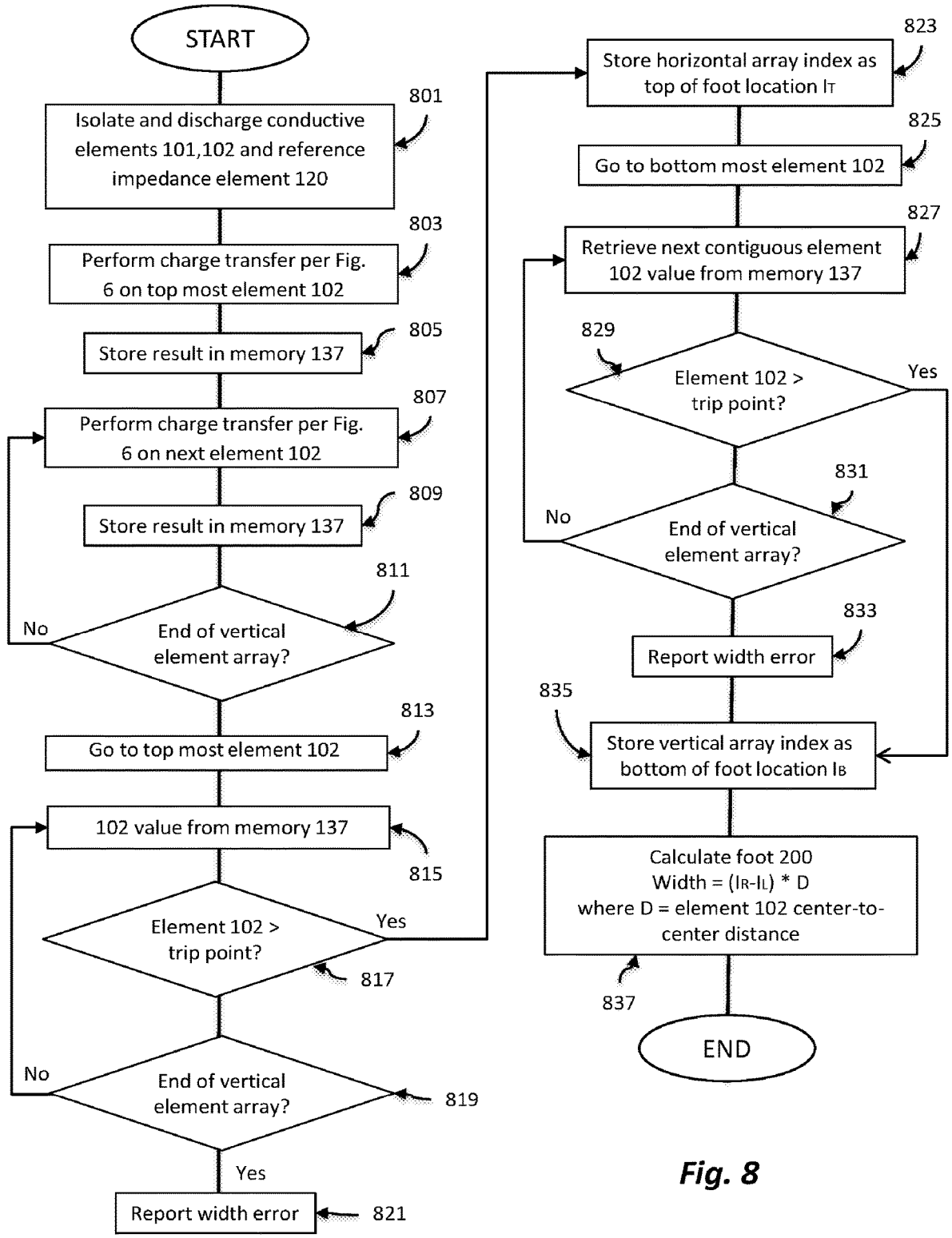
FIG. 8 illustrates a flow diagram of a width measurement algorithm according to the present disclosure.

FIG. 8 is the corollary flow diagram for width measurement. The method begins with isolating and discharging conductive elements 801 and the reference impedance element 120. A charge transfer 803 per FIG. 6 is performed on the first element 102. This result is stored in memory 805. A charge transfer 807 per FIG. 6 is performed on the next element 102, and that result stored 809 in memory. If all elements of the vertical array are not sampled 811, the method reverts to performing a charge transfer (807). Otherwise the method proceeds to the top most element 102 at 813 and retrieves the 102 value from memory 715. When element 102 is greater than a trip point at 817, the method proceeds to store horizontal array index as top of foot location $L_L$ 723. Otherwise the method proceeds through the horizontal array unless there is an error 821. After storing horizontal array index, go to bottom most element 102 at 825, then proceed through elements 102 from memory 827. Again when element 102 is greater than trip point 829, horizontal array index is stored as bottom of foot location $L_R$

735. Otherwise the horizontal array elements are continued to be sampled 731. The foot width is then determined 737 as $L_L$-$L_R$.

Figure 9:
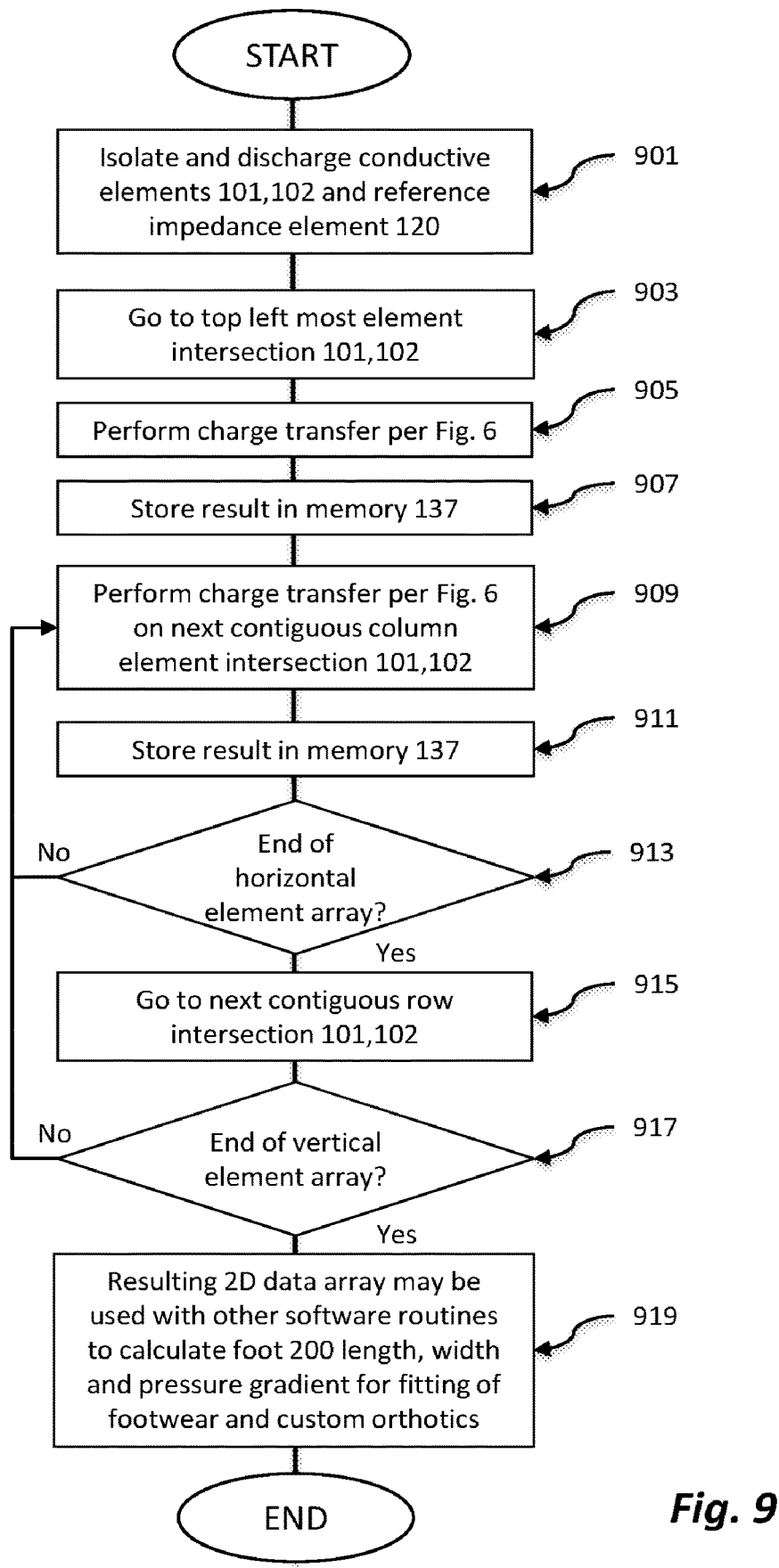
FIG. 9 illustrates a flow diagram of a 2D pressure distribution measurement algorithm according to the present disclosure.

FIG. 9 is a flow diagram of 2D contour and pressure distribution process. The method begins with isolating and discharging conductive elements 901 and the reference impedance element 120. Sampling may be initiated 903 at the top left most element intersection 101, 102. Charge transfer is performed 905 per FIG. 6. This result is stored 907 in memory. Again charge transfer is performed 909 on the contiguous column element intersection 101, 102. These results are stored 911 in memory. After the horizontal array is finished being sampled 913, the next contiguous row intersection 101, 102 is sampled 915. After the vertical element array is completed 917, the resulting 2D data array may be used 919 with other software routines to calculate foot 200 length, width and pressure gradient for fitting of footwear and custom orthotics.

Figure 10:
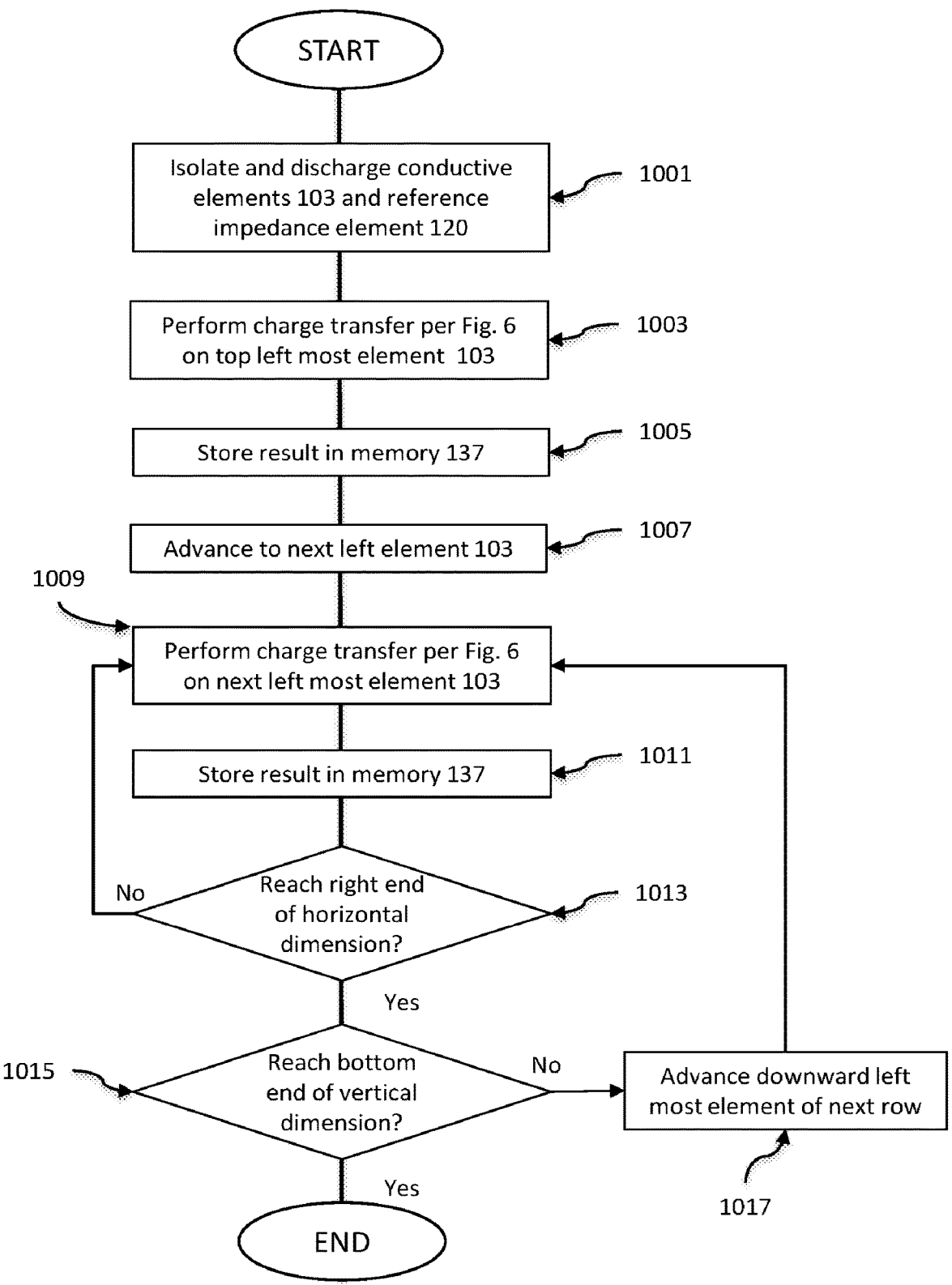
FIG. 10 illustrates a flow diagram of a scan process according to the present disclosure.

FIG. 10 is a flow diagram of a scan process for two-dimensional self-capacitance measurement as may be used with the system of FIG. 5*c*. The method begins with isolating and discharging conductive elements 1001 and the reference impedance element 120. Charge transfer is performed 1003 on top most element 103, and the result stored 1005 in memory. Then the process advances 1007 to the next left (or selected) element 103. Charge transfer is performed 1007 per FIG. 6 on the next element 103 and the result is stored 1011. The process continues until reaching the right end of the horizontal dimension 1013 and then advances down vertically 1017 row by row until reaching the end of the vertical dimension 1015, thereby sampling all elements of the sensor plane 110.

Footwear Applications of the Invention

The embodiments disclosed herein provide methods through which recommendations of an appropriate shoe size for a user may be personalized to allow a purchaser or seller to more accurately select footwear in a brick and mortar store and/or over a computer network, thereby effectively alleviating the possibility that a purchaser may receive and the seller may sell the incorrect shoe size.

The advantages of these embodiments are provided by a system and method for receiving footwear size information for a selected footwear model at a host computer from a client computer over a computer network, such as the Internet. According to the invention, foot size information for the selected footwear model (preferably measured in millimeters) is received from the client computer. Then, a recommended footwear size is determined for the selected footwear model based on the received foot size information generated from any embodiments disclosed herein. Additionally, a length and/or a width adjustment factor can be used for determining the recommended footwear size based e.g., on shoe manufacture recommendations, shoe last data, preference of the wearer, etc.

In one embodiment, the length adjustment factor is determined by selecting, for at least one selected footwear size length, representative footwear from a selected footwear production run for the selected footwear model, such that each representative footwear item may have a different selected footwear size length. An internal dimension is then measured for or otherwise obtained directly from the shoe last data or manufacture for each representative footwear item. An adjusted size length is determined for each respective selected footwear size length as the selected footwear size length minus the average size length for a test subject group when the measured internal dimension for each respective representative footwear test shoe is within a set point, e.g., within about +−0.2 mm of an average internal dimension for the selected footwear size length of the representative footwear for the selected footwear production run of the selected footwear model. The length adjustment factor for the selected production run for the selected footwear model may be determined based on an average of each determined adjusted size length. The width adjust factor is determined in a similar manner.

The received foot size information is converted to a footwear size length, and a recommended footwear size for the selected footwear model is determined by adding the determined length adjustment factor to the converted footwear size length. According to an embodiment of the invention, the recommended footwear size for the selected footwear model can also be based on stored foot size information for a user relating to a selected footwear size for a past footwear product for the user. Information relating to the recommended footwear size for the selected footwear model may then be associated with or stored on a user's device, such as a phone, tablet, computer, data storage unit, cloud or other electronic system or device, and in a most preferred embodiment via an App or software program. In addition or alternatively, information relating to the recommended footwear size for the selected footwear model may then be sent to the client computer over the computer network. Subsequently, information relating to a selected footwear size for the selected footwear model is received from the client computer.

According to another aspect of the invention, the host computer receives a request for information relating to a foot measurement data from the client computer, and sends the information relating to the foot measurement data from the host computer to the client computer. In a most preferred embodiment, the information relating to the foot measurement data provides foot size information in millimeters.

After the user receives the selected footwear, the user may be queried for a fit assessment of the footwear. The information contained in the user's fit assessment includes information relating to at least the previous footwear model and size, a length fit assessment, a width fit assessment, toe room assessment, heel fit assessment, and an overall fit assessment. The fit assessment information is stored in a user profile and used for generating a future recommended shoe size for the user.

According to an embodiment of the invention a communications system in which the computer network-based shoe sizing system of the present invention can be used. This may include an arrangement of networks, components and terminals that include a computer network, such as the Internet, a local area network (LAN), a wide area network (WAN), a public switched telephone network (PSTN), a wireless network, an Internet Service Provider (ISP) and a plurality of terminal devices. Each network may be interconnected with the other networks in a well-known manner. For example, a LAN and a WAN may each be connected to the Internet through gateways, respectively, in a well-known manner. A PSTN and wireless network, such as a cellular telephone network or a personal communication system (PCS), may be connected to the Internet through an ISP in a well-known manner. A PSTN and a wireless network can, of course, be connected directly to the Internet.

A plurality of computer-based terminal devices, such as personal computers (PCS) and hand-held communication devices, may be connected to various computer networks in a well-known manner and operate as client computers. For example, terminal devices may be connected to the Internet by a direct connection to a LAN. Terminal devices may be connected to the Internet by a direction connect to a WAN. A terminal device may be connected to a PSTN by, for example, a modem, and establish a connection to the Internet through an ISP in a well-known manner. Terminal devices may be directly connected to an ISP and, hence, to the Internet. Wireless terminal devices may be connected to a PSTN through a base station (BS) that is part of a wireless network. It should be understood that many terminal devices can be connected to the various networks and components mentioned above. It should also be understood that terminal devices can have a wide range of processing capabilities.

A server may be connected to the Internet in a well-known manner to host what is commonly known as a website. Thus, the server operates as a host computer. Of course, the server can host a single website, or can host a plurality of websites. A computer system and a database may be coupled to the server in a well-known manner. The server receives requests from the Internet for information, such as a webpage, stored within computer system and database. The server receives the requests from a client computer, such as any of the terminal devices referenced above, processes the requests in a well-known manner and passes the requests to the computer system. The computer system, in turn, receives the requests from the server, processes the requests and accesses a database for the specific information requested. Once the information stored in the database has been accessed, the computer system may forward the requested information through the server to the requesting client computer.

It should be understood that the server, computer system and database can be combined into a single computer system performing the respective functions of the server, the computer system and database. Consequently, functionality provided by the server, computer system and database will be referred to herein as a website or host computer. It should also be understood that there may be a plurality of servers connected to the Internet using a variety of well-known techniques. For example, a server can be connected directly to the Internet or can be connected to the Internet, for example, by way of a LAN or a WAN.

Preferably, a computer hosts information and webpages that allow a user to select and purchase footwear or orthotics. For example, a user can request images of specific shoe, sandal and/or boot and/or orthotic models from which to choose, and ordering information, such as pricing and availability. A computer may respond by sending the requested information to the requesting computer. Preferably, a host computer provides an online footwear or orthotic sizing system according to the present invention. As used herein, the terms footwear, orthotic, shoe, sandal and boot are interchangeable.

A process for online sizing of footwear according to the present invention may be accomplished by a user at a client computer, such as terminal device to select a particular footwear model, such as an orthotic, athletic shoe, a dress shoe, a casual shoe, a sandal or a boot. This can be done by any of a plurality of well-known techniques, such as by a user at a client computer "clicking" on an image of a desired footwear model that is visible on the display of the client computer, by the user clicking on the selected model name and/or number, or by the user entering a model name and/or number into a designated field that is visible on the display of the client computer. The selected shoe model can also be custom designed by the user. For example, the user can select color, logos, slogans, shoelace type and color, sole style and color, etc.

The user may send foot-sizing information for the desired model of footwear to a host computer. In order to obtain accurate foot size information (foot length and width in millimeters (mm)), the user can do one of several techniques. First, the user will preferably use the foot size measuring device disclosed herein, or in a less preferable embodiment other technique that may be available on the internet, through applications on a hand held device (e.g., smart phones or tablets), by visiting a shoe retailing location and have the length and width of both feet, measured, along with other foot measurements that include, but are not limited to, ball length, ball girth, instep girth, heel width, instep height, and arch profile.

The footwear sizing system embodiment of the present invention can determine a recommended footwear size preferably based on fit and sizing assessment information for the latest production run of the selected shoe and fit assessment information provided by the user regarding a past footwear product previously selected and obtained through host computer and/or selected and obtained from an associated retail outlet and/or their own physical or electronic system. The past product information can be submitted by the user at the time the new footwear is selected, or can have been submitted at an earlier time. The previously-provided fit assessment information may be stored in a user profile for the user in, for example, a database, and preferably includes the shoe model and shoe size, shoe last information, a length fit assessment, a width fit assessment, toe room assessment, heel fit assessment, and an overall fit assessment. The recommended footwear size for the selected footwear model may be sent from a host computer to a client computer.

The user at client computer may select a desired footwear size for the selected footwear model. The user may select a method of payment in a well-known manner and the order for the selected footwear is placed. In the situation when the selected footwear model and size is in stock or is available for immediate shipment, a fulfillment center associated with host computer may cause shipment of the selected footwear model to the user. In the situation when the selected footwear model is not in stock or available for immediate shipment, then the selected footwear may be fabricated and shipped to the user.

The user may be queried a short while after the shoe is ordered for obtaining the user's fit assessment for the shoe. An e-mail message or text is sent from host computer to a client computer or communication device after the shoe or orthotic is ordered requesting the user to again access the website hosted by host computer and complete a fit assessment survey. The information contained in a completed user fit assessment survey is stored and used for generating a future recommended orthotic or shoe size for the user.

Because the size and fit of a footwear model varies slightly from production run to production run, the present invention utilizes size measurements and fit assessments made for the current production run for each respective footwear model that is available for purchase through a website. The size measurements and fit assessments are then used as a basis for generating a foot size recommendation when foot size information is received from a user.

The IDS (inside dimensions of the shoe) of each of a representative pair of shoes for each production run of the footwear model is measured for selected orthotic or shoe size. For each production run of each orthotic or shoe model, a representative orthotic or pair of shoes is preferably selected, and the IDS is measured for each representative shoe.

The IDS of each representative shoe is compared to the average factory size measurements for the shoe size for the shoe model. If the measured IDS of the representative shoe is not within .+−0.2 mm of the average factory size measurements for the shoe size for the shoe model, then another representative shoe is selected in the same shoe size.

If the measured IDS of the representative shoe is within .+−0.2 mm of the factory size measurements for the shoe size for the shoe model, then the representative shoe becomes a fit trial shoe that will be assessed for fit by a group of human subjects. The Adjusted Size is preferable determined according to the methods and systems disclosed herein for the shoe size to determine the appropriate shoe model.

Human assessment information for each pair of representative shoes is collected. Preferably, human subjects having a measured shoe size corresponding to one of the selected shoe sizes try on the representative shoes and assessment several fit parameters.

Each size category of human subjects then evaluate fit assessment parameters, such as toe box height (TBH), toe box width (TBW), ball girth (BG), waist instep (WI), heel (H), length (L), arch height (AH) and arch position (AP) for both the left and right representative shoes. The fit assessment parameters are preferably evaluated using a scale that ranges from 1 to 9, where 5 is a just right (JR) assessment; 1 is a too low, too narrow, too tight, too short, too far back, etc. assessment; and 9 is a too high, too wide, too loose, too long, too wide, too far forward etc. assessment. Moreover, assessments 1, 2, 8 and 9 are further categorized as a "Fix" type assessment, and assessments 4-6 are further categorized as "Just Right" assessments. The individual fit assessments for each shoe model are tallied for each fit assessment parameter and averaged.

A length adjustment factor (LAF) and a width adjustment factor (WAF) for each shoe model is determined. The foot sizing information, preferably in millimeters, is received from the user. The foot size measurement submitted by the user may be analyzed in view of any previously-provided fit assessment information for a past footwear product that is contained in a profile for the user. Details regarding the analysis of the submitted foot size measurement in view of any previously-provided fit assessment information for a past footwear product that is contained in a profile for the user.

While the present invention has been described as generating a recommended footwear size with the system and methods of the present invention, other footwear sizing standards, such as Brannock-based sizes, European footwear sizes (French Paris point), Japanese (cm scale), Mondo point, UK, cm, can be readily incorporated into the present invention.

The recommended sizing technique of the present invention can also be used for customized footwear sizing, such as selecting the thickness and/or weight of cushioning, footwear uppers features, etc., basing the recommended size on measurements made for the current production run of the selected footwear features (which take into account the manufacturing tolerances for the current production run) and any past product information stored in a profile for the user.

Moreover, the recommended sizing technique of the present invention can be used for generating a recommended size for apparel. Accordingly, a user at a client computer selects a particular garment and supplies size measurements. The host computer then generates a recommended size based on measurements made for the current production run of the selected garment and any past product information stored in a profile for the user. Thus, a host computer can generate a recommended size for pants, shirts, socks, sweaters, coats, belts, etc.

While the present invention has been described in connection with the illustrated embodiments, it will be appreciated and understood that modifications may be made without departing from the true spirit and scope of the invention.

The invention claimed is:

1. A system, comprising:
a set of first orientation conductive elements oriented along a first orientation on a sensor plane;
a reference impedance element;
a controller in communication with a non-transitory memory, a first multiplexer, a second multiplexer and the reference impedance element, wherein the non-transitory memory comprises instructions that, when executed, cause the controller to perform at least the following:
iteratively measuring a set of first orientation conductive element permittivities:
isolate and discharge the reference impedance element,
isolate and charge, to a predetermined positive voltage level, a next first orientation conductive element in the set of first orientation conductive elements,
short the next first orientation conductive element to the reference impedance element for a predetermined time as to allow for charge equalization,
measure a first orientation conductive element permittivity for the next first orientation conductive element,
store the first orientation conductive element permittivity in the set of first orientation conductive element permittivities, and
repeat the iteratively measuring the set of first orientation conductive element permittivities for each first orientation conductive element in the set of first orientation conductive elements; and
generating a permittivity profile of an object in contact with the sensor plane based at least in part on the set of first orientation conductive element permittivities.

2. The system of claim 1, wherein the controller is further configured to perform at least the following:
measure a voltage of a charge transfer from the next first orientation conductive element to the reference impedance element caused by the short; and
determine, based on the voltage, the first orientation conductive element permittivity.

3. The system of claim 1, further comprising:
a first multiplexer configured to activate each first orientation conductive element in the set of first orientation conductive elements; and
wherein the instructions, when executed, further cause at least the following:
control the first multiplexer to isolate and charge the next first orientation conductive element in the set of first orientation conductive elements.

4. The system of claim 1, wherein the controller is further configured to perform at least the following:
determine a first spacing between each first orientation conductive element in the set of first orientation conductive elements;
determine a first scan trip point based on a first next first orientation conductive element in the set of first orientation conductive elements having an associated first orientation conductive element permittivity greater than a predetermine trip point;

determine a last scan trip point based on a last next first orientation conductive element in the set of first orientation conductive elements having an associated first orientation conductive element permittivity greater than a predetermine trip point;

determine a number of first orientation conductive elements between the first next first orientation conductive element and the last next first orientation conductive element; and determine a first dimension of the object based at least in part on the number of first orientation conductive elements and the first spacing.

5. The system of claim 1, further comprising:
a set of second orientation conductive elements oriented along a second orientation on the sensor plane;
wherein the second orientation is different from the first orientation;
wherein the instructions, when executed, further cause at least the following:
iteratively measuring a set of second orientation conductive element permittivities:
isolate and discharge the reference impedance element,
isolate and charge a next second orientation conductive element in the set of second orientation conductive elements,
short the next second orientation conductive element to the reference impedance element,
measure a second orientation conductive element permittivity for the next second orientation conductive element,
store the second orientation conductive element permittivity in the set of second orientation conductive element permittivities, and
repeat the iteratively measuring the set of second orientation conductive element permittivities for each second orientation conductive element in the set of second orientation conductive elements; and
generating the permittivity profile of the object based at least in part on the set of first orientation conductive element permittivities and the set of second orientation conductive element permittivities.

6. The system of claim 5, wherein the first orientation and the second orientation are orthogonal.

7. The system of claim 5, further comprising:
a first multiplexer configured to activate each first orientation conductive element in the set of first orientation conductive elements;
a second multiplexer configured to activate each second orientation conductive element in the set of second orientation conductive elements; and
wherein the instructions, when executed, further cause at least the following:
control the first multiplexer to isolate and charge the next first orientation conductive element in the set of first orientation conductive elements, and
control the second multiplexer to isolate and charge the next second orientation conductive element in the set of second orientation conductive elements.

8. The system of claim 5, wherein the controller is further configured to perform at least the following:
determine a first spacing between each first orientation conductive element in the set of first orientation conductive elements;

determine a first horizontal scan trip point based on a first next first orientation conductive element in the set of first orientation conductive elements having an associated first orientation conductive element permittivity greater than a predetermine trip point;

determine a last horizontal scan trip point based on a last next first orientation conductive element in the set of first orientation conductive elements having an associated first orientation conductive element permittivity greater than a predetermine trip point;

determine a number of first orientation conductive elements between the first next first orientation conductive element and the last next first orientation conductive element;

determine a length of the object based at least in part on the number of first orientation conductive elements and the first spacing;

determine a second spacing between each second orientation conductive element in the set of second orientation conductive elements;

determine a first vertical scan trip point based on a second next second orientation conductive element in the set of second orientation conductive elements having an associated second orientation conductive element permittivity greater than a predetermine trip point;

determine a last vertical scan trip point based on a last next second orientation conductive element in the set of second orientation conductive elements having an associated second orientation conductive element permittivity greater than a predetermine trip point;

determine a number of second orientation conductive elements between the second next second orientation conductive element and the last next second orientation conductive element; and determine a width of the object based at least in part on the number of second orientation conductive elements and the second spacing.

9. The system of claim 5, wherein the controller is further configured to perform at least the following:
determine permittivity changes for a particular next first orientation conductive element, comprising:
remeasuring the first orientation conductive element permittivity for the particular next first orientation conductive element while the iteratively measuring the set of second orientation conductive element permittivities.

10. The system of claim 9, wherein the controller is further configured to perform at least the following:
determine a pressure value based on each permittivity change; and
generate a pressure value map based on the permittivity changes.

11. A method, comprising:
iteratively measuring, by at least one processor, a set of first orientation conductive element permittivities comprising:
isolating and dischargeing a reference impedance element,
isolating and charging, to a predetermined positive voltage level, a next first orientation conductive element in a set of first orientation conductive elements,
wherein the set of first orientation conductive elements are on a sensor plane,
shorting the next first orientation conductive element to the reference impedance element for a predetermined time as to allow for charge equalization, measuring a first orientation conductive element permittivity for the next first orientation conductive element, storing the first orientation conductive element permittivity in a set of first orientation conductive element permittivities, repeating the iteratively measuring the set of first orientation conductive element permittivities for each first orientation conductive element in the set of first orientation conductive elements;

wherein the set of first orientation conductive element permittivities are oriented in a first orientation along a sensor plane; and generating, by the at least one processor, a permittivity profile of an object in contact with the sensor plane based at least in part on the set of first orientation conductive element permittivities.

12. The method of claim 11, further comprising:

measuring, by the at least one processor, a voltage of a charge transfer from the next first orientation conductive element to the reference impedance element caused by the short; and determining, by the at least one processor, based on the voltage, the first orientation conductive element permittivity.

13. The method of claim 11, further comprising:

controlling, by the at least one processor, a first multiplexer to isolate and charge the next first orientation conductive element in the set of first orientation conductive elements.

14. The method of claim 11, further comprising:

determining, by the at least one processor, a first spacing between each first orientation conductive element in the set of first orientation conductive elements;

determining, by the at least one processor, a first scan trip point based on a first next first orientation conductive element in the set of first orientation conductive elements having an associated first orientation conductive element permittivity greater than a predetermine trip point;

determining, by the at least one processor, a last scan trip point based on a last next first orientation conductive element in the set of first orientation conductive elements having an associated first orientation conductive element permittivity greater than a predetermine trip point;

determining, by the at least one processor, a number of first orientation conductive elements between the first next first orientation conductive element and the last next first orientation conductive element; and determining, by the at least one processor, a first dimension of the object based at least in part on the number of first orientation conductive elements and the first spacing.

15. The method of claim 11, further comprising:

iteratively measuring, by at least one processor, a set of second orientation conductive element permittivities comprising:

isolating and discharging a reference impedance element, isolating and charging a next second orientation conductive element in a set of second orientation conductive elements, wherein the set of second orientation conductive elements are on a sensor plane, shorting the next second orientation conductive element to the reference impedance element, measuring a second orientation conductive element permittivity for the next second orientation conductive element, storing the second orientation conductive element permittivity in a set of second orientation conductive element permittivities, repeating the iteratively measuring the set of second orientation conductive element permittivities for each second orientation conductive element in the set of second orientation conductive elements;

wherein the set of second orientation conductive element permittivities are oriented in a second orientation along a sensor plane; and generating, by the at least one processor, the permittivity profile of the object in contact with the sensor plane based at least in part on the set of first orientation conductive element permittivities and the set of second orientation conductive element permittivities.

16. The method of claim 15, wherein the first orientation and the second orientation are orthogonal.

17. The method of claim 15, further comprising:

controlling, by the at least one processor, a first multiplexer to isolate and charge the next first orientation conductive element in the set of first orientation conductive elements, and controlling, by the at least one processor, a second multiplexer to isolate and charge the next second orientation conductive element in the set of second orientation conductive elements.

18. The method of claim 15, further comprising:

determining, by the at least one processor, a first spacing between each first orientation conductive element in the set of first orientation conductive elements;

determining, by the at least one processor, a first horizontal scan trip point based on a first next first orientation conductive element in the set of first orientation conductive elements having an associated first orientation conductive element permittivity greater than a predetermining trip point;

determining, by the at least one processor, a last horizontal scan trip point based on a last next first orientation conductive element in the set of first orientation conductive elements having an associated first orientation conductive element permittivity greater than a predetermining trip point;

determining, by the at least one processor, a number of first orientation conductive elements between the first next first orientation conductive element and the last next first orientation conductive element;

determining, by the at least one processor, a length of the object based at least in part on the number of first orientation conductive elements and the first spacing;

determining, by the at least one processor, a second spacing between each second orientation conductive element in the set of second orientation conductive elements;

determining, by the at least one processor, a first vertical scan trip point based on a second next second orientation conductive element in the set of second orientation conductive elements having an associated second orientation conductive element permittivity greater than a predetermining trip point;

determining, by the at least one processor, a last vertical scan trip point based on a last next second orientation conductive element in the set of second orientation conductive elements having an associated second orientation conductive element permittivity greater than a predetermining trip point;

determining, by the at least one processor, a number of second orientation conductive elements between the second next second orientation conductive element and the last next second orientation conductive element; and determining, by the at least one processor, a width of the object based at least in part on the number of second orientation conductive elements and the second spacing.

19. The method of claim 15, further comprising determining, by the at least one processor, permittivity changes for a particular next first orientation conductive element, comprising:

remeasuring the first orientation conductive element permittivity for the particular next first orientation conductive element while the iteratively measuring the set of second orientation conductive element permittivities.

20. The method of claim 19, further comprising:

determining, by the at least one processor, a pressure value based on each permittivity change; and generating, by the at least one processor, a pressure value map based on the permittivity changes.

* * * * *